United States Patent
Sudor

(10) Patent No.: US 7,449,304 B2
(45) Date of Patent: Nov. 11, 2008

(54) METHOD FOR ENHANCING THE EFFICIENCY OF AN ENZYMATIC PROCESS FOR REMOVAL OF CONTAMINATING NUCLEOTIDES

(75) Inventor: Jan Sudor, Grenoble (FR)

(73) Assignee: Serono Genetics Institute S.A., Evry (FR)

( * ) Notice: Subject to any disclaimer, the term of this patent is extended or adjusted under 35 U.S.C. 154(b) by 365 days.

(21) Appl. No.: 10/493,976

(22) PCT Filed: Oct. 14, 2002

(86) PCT No.: PCT/IB02/04624
§ 371 (c)(1),
(2), (4) Date: Jul. 6, 2005

(87) PCT Pub. No.: WO03/042391

PCT Pub. Date: May 22, 2003

(65) Prior Publication Data

US 2006/0057681 A1    Mar. 16, 2006

Related U.S. Application Data

(60) Provisional application No. 60/332,580, filed on Nov. 13, 2001.

(51) Int. Cl.
*C12Q 1/42* (2006.01)
(52) U.S. Cl. .................................................. 435/21
(58) Field of Classification Search .................. None
See application file for complete search history.

(56) References Cited

FOREIGN PATENT DOCUMENTS

| WO | WO 01/68913 A2 | 9/2001 |
|----|----------------|--------|
| WO | WO 02/30571 A2 | 4/2002 |

*Primary Examiner*—Irene Marx
*Assistant Examiner*—Satyendra K Singh
(74) *Attorney, Agent, or Firm*—Saliwanchik, Lloyd & Saliwanchik

(57) ABSTRACT

This invention relates to methods for enhancing the efficiency of biological processes that involve successive enzymatic reactions. More specifically, the invention relates to methods for enhancing the efficiency of an enzymatic purification process by increasing the temperature between successive enzymatic purification steps.

15 Claims, No Drawings

METHOD FOR ENHANCING THE EFFICIENCY OF AN ENZYMATIC PROCESS FOR REMOVAL OF CONTAMINATING NUCLEOTIDES

CROSS-REFERENCE TO RELATED APPLICATION

This application is the U.S. national stage application of International Patent Application No. PCT/IB02/04624, filed Oct. 14, 2002, which claims the benefit of U.S. Provisional Patent Application Number 60/332,580, filed Nov. 13, 2001.

FIELD OF THE INVENTION

This invention relates to a method for enhancing the efficency of an enzymatic purification process, e.g., by increasing the temperature between successive enzymatic purification steps.

BACKGROUND

When fluid operations are performed in small reaction plates such as microtiter plates, typically one biological reaction is carried out in each well of the plate. Some processes, however, require successive reactions, the reactants or products of one or more of which may be incompatible with subsequent reactions, thereby necessitating the introduction of intervening processes in which such undesired reactants or products are removed or inactivated. For example, genotyping process by the single base extension method requires three biological reactions (i.e., polymerase chain reaction (PCR), enzymatic purification and microsequencing (MIS)). It is efficient and beneficial to perform two or more of these successive reactions in the same well of one unique microtiter plate, a major problem with performing successive reactions in a single well, however, is inter-reaction contamination, i.e., the contamination of subsequent reactions by biomolecules from previous reactions.

For example, one commonly encountered problem in genotyping is contamination by deoxynucleotides (dNTPs) left over from amplification reactions such as PCR of subsequent reactions, such as microsequencing. To address this problem, an enzymatic purification step is typically performed, in which enzymes such as alkaline phosphatase are added to remove dNTPs left over from the PCR. The efficiency of such enzymatic purification reactions is critical, as any dNTPs present in the microsequencing reaction can extend the microsequencing primer beyond the SNP site, thereby allowing the labeled ddNTP to be incorporated downstream of the SNP, leading to errors in genotyping. Similar problems may be encountered in any process involving successive enzymatic reactions. To overcome such problems, the duration of the enzymatic purification step may be extended, the amount of alkaline phosphatase may be increased, or the reaction mixture may be transferred between successive reaction steps, yet in practice none of these potential solutions has been successful in eliminating the problem of contamination.

Clearly, there is a great need in the art for novel methods of decreasing contamination of successive reactions within experimental biological processes. The present invention addresses these and other needs.

DESCRIPTION

The present invention provides novel methods for increasing the efficiency of biological processes that involve successive enzymatic reactions, in particular wherein the presence of one or more reactants or products of one reaction is deleterious for one or more subsequent reactions. The present invention is based upon the discovery that a primary impediment to previous methods used to eliminate inter-reaction contamination, such as enzymatic purification methods, is the adsorption of potential contaminants to hydrophobic surfaces or to air/liquid or liquid/liquid interfaces. This adsorption decreases the accessibility of the contaminants to the agents (e.g. enzymes) used to eliminate them, thereby decreasing the efficiency of the decontamination process. For example, adsorption of dNTPs added during the first step of a genotyping procedure (e.g., PCR) onto the surface of a microtiter plate render them less accessible to alkaline phosphatase (e.g., SAP) during a subsequent enzymatic purification step, and the adsorbed dNTPs are therefore not dephosphorylated. As dNTPs release from the surface of the microtiter plate at high temperature (e.g., during the denaturation of EXO and SAP enzymes or during the temperature cycling of the MIS reactions), they can dramatically contaminate the third step of the genotyping process (i.e., MIS). In addition, adsorption of biomolecules onto the surface of a microtiter plate often leads to a reduced yield of biological reactions. This contamination and reduced yield becomes even more significant when reactions are performed in very small volumes (e.g., high-density plates), as the number of interactions of molecules from bulk solution with surfaces increases rapidly when the reaction volume decreases.

In some situations, reaction mixtures are transferred into a new microtiter plate between the two successive reactions. For example, in the case of a genotyping process, PCR may be performed in one microtiter plate and enzymatic purification followed by MIS is performed in another microtiter plate. However, while this represents an improvement over traditional methods wherein all reactions are performed in a single well, this method is not completely effective in eliminating contamination, as many MIS reactions are nevertheless contaminated by leftover dNTPs from PCR reactions. Also, the transfer of samples reduced the yield of MIS reactions. Furthermore, it is technically more convenient and cheaper to use a method that does not require the transfer of samples to a new microtiter plate.

To overcome the above-described problems, the present invention provides a novel method of performing processes, such as enzymatic purification, wherein an additional, increased temperature step, is introduced into the process. This increased temperature step promotes the desorption of reactants and products from surfaces and interfaces, thereby increasing the efficiency of the process.

Accordingly, the present invention involves a method of enhancing the efficiency of an enzymatic purification process. This method is useful for decreasing adsorption of a reactant or a product left-over from an earlier-performed fluid operation to a surface or interface during enzymatic purification by increasing the temperature, thereby increasing the accessibility of said reactant or said product to the enzyme and facilitating its destruction or inactivation.

The invention further includes general methods for performing biological processes on surfaces such that the adsorption of undesired components of one or more steps of the process to a surface or interface is minimized by increasing the temperature between the steps. In other words, the process, which typically involves one or more unrepeated steps, is now performed in a cyclic manner, wherein each cycle involves an additional step in which the temperature is raised above the optimal temperature for the other, previously-unrepeated steps. In this way, the adsorption of certain components of the process to the a hydrophobic surface, e.g. the surface of a microwell plate, or to an interface, e.g. an air/air or air/liquid interface, is reduced. These biological processes can include, but are not limited to, reactions, incubations, dilutions, titrations, purifications, detections, mixing and drug screening assays. Further, in certain embodiments, this cyclic process involving an elevated temperature step may be performed prior or subsequent to other biological processes, such as amplification reactions, sequencing reactions, or genotyping methods such as microsequencing or primer extension reactions. It will be appreciated, however, that the cyclic biological process comprising the elevated temperature step is not Polymerase Chain Reaction (PCR).

In a first aspect, the invention encompasses a method of enhancing the efficiency of an enzymatic purification process, said method comprising the following steps: a) incubating on a hydrophobic surface a reaction mixture comprising a reactant or product from an earlier-performed reaction and an enzyme capable of destroying or inactivating said reactant or said product, at a first temperature which is optimal for the activity of said enzyme; b) raising the temperature of said reaction mixture to a second temperature which is higher than said first temperature but at which a substantial amount of said enzyme is not denatured, thereby decreasing the adsorption of said reactant or said product to said surface and thereby increasing its accesibility to said enzyme; c) repeating steps a) and b) until a desired amount of said reactant or said product has been destroyed or inactivated; and, optionally, d) raising the temperature of said reaction mixture to a third temperature which is sufficient to denature said enzyme. It will be appreciated, that the enzymatic purification process is not Polymerase Chain Reaction (PCR).

In another aspect, the invention encompasses a method of enhancing the efficiency of an enzymatic purification process, said method comprising the following steps: a) incubating a reaction mixture comprising a reactant or product from an earlier-performed reaction and an enzyme capable of destroying or inactivating said reactant or said product, at a first temperature which is optimal for the activity of said enzyme; b) raising the temperature of said reaction mixture to a second temperature which is higher than said first temperature but at which a substantial amount of said enzyme is not denatured, thereby decreasing the adsorption of said reactant or said product to the interface air/liquid or liquid/liquid and thereby increasing its accesibility to said enzyme; c) repeating steps a) and b) until a desired amount of said reactant or said product has been destroyed or inactivated; and d) raising the temperature of said reaction mixture to a third temperature which is sufficient to denature said enzyme. It will be appreciated that all of the above-described embodiments apply equally to this aspect of the invention as well.

In another aspect, the invention encompasses a method of optimizing an enzymatic purification process, comprising the steps of: a) performing said enzymatic purification process involving the reactant or the product on a surface; b) increasing the temperature of said enzymatic purification process to a variety of temperatures; c) repeating steps a) and b); d) determining the level of said reactant or said product adsorbed to the surface of said surface or the yield of said enzymatic purification process; and e) determining said optimal temperature for obtaining the lowest amount of adsorption of said reactant or said product to said surface or the highest yield of said enzymatic purification process. In another aspect, the present invention provides a method of determining a temperature for optimizing an enzymatic purification process, comprising the steps of a) performing the above-described method of enhancing the efficiency of an enzymatic purification reaction a plurality of times, wherein for each of these times the second temperature is different; b) comparing the relative level of the reactant or product remaining in each of the reaction mixtures at the end of each time; and c) determining the second temperature at which the remaining level of reactant or product is the lowest.

For any of the present aspects of the invention, in one embodiment, the surface is made of any of a wide variety of materials, including, but not limited to, silicon, plastic, quartz, glass, ceramics, or any combination of any of these or other materials. Preferably said plastic is a hydrophobic polymer, such as polystyrene, polypropylene, polymethyl methacrylate, polyvinyl chloride, polymethyl penten, polyethylene, polycarbonate, polysulfone, polystyrene, fluoropolymers, polyamides, silicones and elastomers. In another embodiment, the hydrophobic surface is part of a microtiter plate, a microfluidics device, a test tube, multi-well plate, reaction well, or eppendorf tube. Preferably, the microtiter plate is a prolypropylene microtiter plate. Microtiter plates of the invention preferably are high density microtiter plates, such as microtiter plates having 96,384,1536 or more wells.

In another embodiment, the reactant or product is a biological compound (including natural or non-natural compounds which may be used in a biological reaction such as any molecular biological method), such as a dNTP or ddNTP. In another embodiment, the earlier-performed reaction is an amplification reaction and the enzyme is alkaline phosphatase, e.g. shrimp alkaline phosphatase. In another embodiment, the method further comprises the step of performing on the hydrophobic surface a subsequent reaction comprising the reaction mixture, wherein said reaction is inhibited by the presence of said reactant or said product. In one such embodiment, the subsequent reaction is a genotyping reaction, such as a microsequencing reaction. In a preferred embodiment, each of these reactions (e.g. the previous and subsequent reactions, as well as the process encompassed by the present methods), are performed on a single surface, e.g. in a single well, tube, or channel. In yet another embodiment, reaction mixture in volume is less than 50, 40, 30, 20, 15, 10, 8, 5, 4, 3, 2 or 1 microliter. In further embodiment, the first temperature is 37 degrees C. In another preferred embodiment, the second temperature is at least 10 degrees higher than said first temperature. In a preferred embodiment, the third temperature is 94 degrees C.

The present invention also provides kits, devices, and apparati for performing the herein-described methods.

Another possibility for preventing contamination, which may be used in conjunction with the present methods, is to coat the surface with a polymer in order to prevent adsorption of valuable biomolecules, as described in PCT/US01/42631, the entire teachings of which are herein disclosed by reference.

What is claimed:

1. A method of enhancing the efficiency of an enzymatic process for removal of contaminating dNTPs or ddNTPs in a reaction mixture comprising:

a) incubating on a hydrophobic surface a reaction mixture comprising a reactant or product and a contaminant comprising dNTPs or ddNTPs from an earlier-performed reaction selected from the group consisting of an amplification reaction, sequencing reaction and genotyping reaction, and an enzyme that removes or inactivates said contaminant at a first temperature which is optimal for the activity of said enzyme;

b) raising the temperature of said reaction mixture to a second temperature which is higher than said first temperature to promote desorption of said contaminant from said surface and thereby increasing its accessibility to said enzyme, wherein a substantial amount of said enzyme is not denatured at said second temperature;

c) repeating steps a) and b) to reduce the amount of contaminant in said reaction mixture; and d) raising the temperature of said reaction mixture from step c) to a third temperature to inactivate or denature said enzyme;

wherein said enzyme is alkaline phosphatase.

2. The method of claim 1, further comprising the step of performing on said hydrophobic surface a subsequent reaction comprising said reaction mixture from step d), wherein said subsequent reaction is inhibited by the presence of said contaminant.

3. The method of claim 1, wherein said hydrophobic surface is part of a microtiter plate or microfluidics device.

4. The method of claim 1, wherein the volume of said reaction mixture is less than 50, 40, 30, 20, 15, 10, 8, 5, 4, 3, 2 or 1 microliter.

5. The method of claim 1, wherein said first temperature is 37 degrees C.

6. The method of claim 1, wherein said second temperature is at least 10 degrees C. higher than said first temperature, wherein a substantial amount of said enzyme is not denatured at said second temperature.

7. The method of claim 1, wherein said third temperature is 94 degrees C.

8. A method of reducing the amount of unreacted dNTPs or ddNTPs in a PCR reaction mixture comprising:

a) incubating a reaction mixture comprising dNTPs or ddNTPs and alkaline phosphatase at a first temperature;

b) raising the temperature of said reaction mixture to a second temperature which is higher than said first temperature to promote desorption of said dNTPs or ddNTPs from a hydrophobic surface or an interface to increase the accessibility of said dNTPs or ddNTPs to said alkaline phosphatase and allow for the dephosphorylation of said dNTPs or said ddNTPs;

c) repeating steps a) and b) to reduce the amount of said dNTPs or ddNTPs in said reaction mixture; and d) raising the temperature of said reaction mixture to a third temperature to inactivate or denature said alkaline phosphatase.

9. The method of claim 8, further comprising the step of performing a subsequent reaction using said reaction mixture from step d), wherein said subsequent reaction is inhibited by the presence of said dNTPs or said ddNTPs.

10. The method of claim 9, wherein said subsequent reaction is an amplification reaction.

11. The method of claim 8, wherein said hydrophobic surface is a microtiter plate or microfluidics device.

12. The method of claim 8, wherein the volume of said reaction mixture is less than 50, 40, 30, 20, 15, 10, 8, 5, 4, 3, 2 or 1 microliter.

13. The method of claim 8, wherein said first temperature is 37 degrees C.

14. The method of claim 8, wherein said second temperature is at least 10 degrees C. higher than said first temperature, and wherein said second temperature allows dephosphorylation of said dNTPs or said ddNTPs.

15. The method of claim 8, wherein said third temperature is 94 degrees C.

* * * * *